(12) United States Patent
Bluth et al.

(10) Patent No.: US 6,511,435 B1
(45) Date of Patent: Jan. 28, 2003

(54) BLOOD PRESSURE MEASUREMENT SYSTEM

(75) Inventors: Charles Bluth, Incline Village, NV (US); James Bluth, Verdi, NV (US)

(73) Assignee: Computerized Screening, Inc., Sparks, NV (US)

( * ) Notice: Subject to any disclaimer, the term of this patent is extended or adjusted under 35 U.S.C. 154(b) by 0 days.

(21) Appl. No.: 09/549,840

(22) Filed: Apr. 14, 2000

(51) Int. Cl.$^7$ ................................................ A61B 5/00
(52) U.S. Cl. ........................ 600/490; 600/493; 600/494; 600/495; 600/496
(58) Field of Search ........................... 600/481, 485–504

(56) References Cited

U.S. PATENT DOCUMENTS

| | | | |
|---|---|---|---|
| 4,677,983 A | * | 7/1987 | Yamaguchi et al. ......... 600/493 |
| 4,998,534 A | * | 3/1991 | Claxton, III et al. ....... 600/493 |
| 5,054,495 A | * | 10/1991 | Uemura et al. ............. 600/493 |
| 5,140,991 A | | 8/1992 | Niwa ......................... 128/687 |
| D371,844 S | * | 7/1996 | Sadritabrizi et al. ....... D24/165 |
| 5,533,511 A | * | 7/1996 | Kaspari et al. ......... 600/494 X |
| 5,647,369 A | * | 7/1997 | Petrucelli et al. ....... 600/485 X |
| 5,704,362 A | * | 1/1998 | Hersh et al. ................ 600/486 |

FOREIGN PATENT DOCUMENTS

| | | | |
|---|---|---|---|
| EP | 0 422 512 | 4/1991 | ........... A61B/5/022 |
| WO | WO 95/18564 | 7/1995 | ........... A61B/5/00 |

OTHER PUBLICATIONS

PCT Written Opinion for Application No. PCT/US01/12082, Jan. 25, 2002 (8 pages).

* cited by examiner

*Primary Examiner*—Robert L. Nasser
(74) *Attorney, Agent, or Firm*—Skjerven Morrill LLP (57) ABSTRACT

A blood pressure measurement device and associated operating method utilize a measurement algorithm based on a plurality of measurements, supplying a unique ability to increase diagnostic and analytical success in detection. In an illustrative implementation, three measurement techniques are used in combination to improve overall measurement accuracy. A first of the three techniques is an ascultatory technique. A sound measurement acquired from a microphone located in the measurement cuff detects start and end Korotkoff sounds using a combination of filters. The auscultatory technique is a conventional method that is recommended by the American Heart Association and is similar to manual techniques used by a nurse or technician. The auscultatory technique and associated filtering techniques are well known by those having ordinary skill in the art. A second technique is an oscillometric technique that is commonly found in many low-cost blood pressure measurement devices. A pressure cuff is used to measure pressure oscillations, which are detected and monitored using mean pressure, and systolic and diastolic pressure ratios to identify systolic and diastolic blood pressure. A third technique, called a pattern recognition technique, measures a sound envelope and incorporates pattern recognition to identify systolic and diastolic pressures. A signal from the pressure sensor is used in addition to the three techniques to quantify the regions of sound under analysis.

29 Claims, 10 Drawing Sheets

BLOOD PRESSURE MEASUREMENT SYSTEM

BACKGROUND OF THE INVENTION

The field of medicine has long employed health care screening to diagnose and tract patients' health. An annual physical examination is a well-known part of patient medical care.

A number of portable monitoring devices are used in medical monitoring. One well known device is the so-called Holter monitor which is an EKG monitor which typically uses a magnetic tape recorder to record EKG signals from a patient over extended periods of time. Another is a monitor for obtaining blood pressure readings over extended periods of time.

Hospitals, health clinics, and pharmacies, in addition to an active role is supplying medical supplies and pharmaceuticals, have actively promoted various health care screenings and wellness programs. Programs are sometimes offered with the help of other health care providers or coordinated on a national basis with groups such as the American Lung Association, the American Diabetes Association and the American Podiatric Medical Association.

Health care screening devices in hospitals, physician's offices, businesses, and the like, in combination with the growing number of home diagnostic kits that are available have increased the efficiencies in health care delivery. Chain drug store operators have increasingly encouraged individual testing by making available in-store diagnostic testing devices. For example, a pharmacist who fills a high-blood pressure medicine for a customer may encourage the customer to regularly check blood pressure. The customer may use a blood pressure measurement and screening device in the drug store.

The offer of in-store testing commonly is highly popular among customers and greatly boosts the number of people visiting the store. In-store testing is valuable for positioning stores as health and wellness centers as well as retailers of health care products. In-store testing increases sales since a consumer who learns of a health problem through screening in the store has some likelihood of purchasing a home test kit to monitor the problem. For example, a customer who discovers a problem of high blood pressure through an in-store test is a likely candidate to purchase a home test kit.

In-store health care screening expands the pharmacist's role in patient care through education. Test device manufacturers have advanced the design and functionality of products to simplify usage and improve accuracy. The challenge for further improvements in health care screening is to educate consumers about the need for medical tests, and demonstrate that many tests are effectively performed by publicly available devices or at home.

A present concern is that health screening is performed on an insufficient segment of the population to efficiently prevent or treat ailments. Other concerns are that health screening is too costly, limited in scope, and time-consuming both for individual patients and health care providers. Despite these deficiencies, a strong awareness exists of a need and desire for improved health screening procedures and equipment. Health care providers, insurance companies, and employers that ultimately pay for health care have encouraged development and usage of improved, accurate yet economic health screening facilities both for treatment and prevention of health care problems.

Generally individual doctors and small groups of doctors have insufficient capital to maintain a complete health screening facility. Even if more health care providers were suitably equipped, typically only a small part of the population exploits health screening facilities due to time and cost considerations and apathy.

What are needed are health screening devices, facilities, and methods that can be placed in locations that are convenient to health care customers. Suitable locations include retail outlets such as pharmacies or drug stores where customers already make health care purchases, but also include medical offices or hospitals, convalescence and elderly care homes, work places such as offices or factory sites, college dormitories, and the like. What are further needed are health screening devices, facilities, and methods that are convenient, efficient, low in cost, and professionally accurate in screening health care data.

SUMMARY

A blood pressure measurement device and associated operating method utilize a measurement algorithm based on a plurality of measurements, supplying a unique ability to increase diagnostic and analytical success in detection. In an illustrative implementation, three measurement techniques are used in combination to improve overall measurement accuracy. A first of the three techniques is an ascultatory technique. A sound measurement acquired from a microphone located in the measurement cuff detects start and end Korotkoff sounds using a combination of filters. The auscultatory technique is a conventional method that is recommended by the American Heart Association and is similar to manual techniques used by a nurse or technician. The auscultatory technique and associated filtering techniques are well known by those having ordinary skill in the art. A second technique is an oscillometric technique that is commonly found in many low-cost blood pressure measurement devices. A pressure cuff is used to measure pressure oscillations, which are detected and monitored using mean pressure, and systolic and diastolic pressure ratios to identify systolic and diastolic blood pressure. A third technique, called a pattern recognition technique, measures a sound envelope and incorporates pattern recognition to identify systolic and diastolic pressures. A signal from the pressure sensor is used in addition to the three techniques to quantify the regions of sound under analysis.

The combination of measurement techniques produce multiple measurements that are combined using a voting technique to identify and discard improper results. Remaining measurements are averaged to within a predefined tolerance to improve the final results. Use of additional measurement techniques improve the measurement accuracy.

The ascultatory technique employs Korotkoff sounds to determine systolic and diastolic pressure points to determine measurement cycle timing. The oscillometric technique senses and monitors oscillations in a pressure waveform to locate systolic and diastolic pressures. A pattern analysis technique senses a pressure envelope and monitors the pressure envelope to locate characteristic changes in a sound envelope to determine systolic and diastolic pressures.

In some embodiments, the blood pressure measurement device includes a controller for controlling a pressure cuff to inflate the cuff in preparation for a blood pressure measurement and to slowly deflate, or bleed, the cuff to determine systolic and diastolic pressures and to generate a pressure waveform.

In accordance with one aspect of the present invention, a test apparatus includes an ascultatory analyzer, an oscillometric analyzer, and a pattern recognition analyzer. The ascultatory analyzer is capable of sensing and analyzing an audio signal using Korotkoff sounds to determine a systolic pressure and a diastolic pressure. The oscillometric analyzer is capable of sensing and analyzing oscillations of a pressure signal to determine the systolic pressure and the diastolic pressure. The pattern recognition analyzer is capable of sensing a pressure envelope and monitoring the envelope pattern to locate characteristic changes and thereby identify systolic and diastolic pressures. A comparing block compares the parameters measured using the distinct measurement techniques, determines mutually consistent limits for the distinct measurement techniques, and rejects measurement samples outside the determined limits. Results produced by the distinct measurement techniques are combined to quantify an optimal systolic pressure result and an optimal diastolic pressure result.

In accordance with another aspect of the blood pressure measurement device and operating method, a blood pressure measurement system includes a kiosk, a blood pressure interface coupled to the kiosk and capable of detecting a pressure signal, a microphone coupled to the blood pressure interface and capable of detecting an audio signal, and a blood pressure analyzer coupled to the kiosk, the blood pressure interface, and the microphone. The blood pressure analyzer includes a plurality of separate analyzers that detect blood pressure using a plurality of separate analysis techniques, the plurality of analysis techniques being based on analysis of audio signals, pressure oscillations, and pattern recognition of a pressure envelope.

In accordance with another aspect of the blood pressure measurement device, a method of measuring blood pressure of a test subject includes acquisition of at least three distinct measurement techniques that measure a plurality of physiological parameters. A first technique is an auscultatory technique including sensing an audio signal and analyzing the audio signal using an ascultatory analysis of Korotkoff sounds to determine a systolic pressure and a diastolic pressure. A second technique is an oscillometric technique including sensing pressure oscillations and analyzing the pressure oscillations using an oscillometric analysis to determine mean pressure, systolic and diastolic blood pressure, and to identify systolic and diastolic pressures. A third technique is a pattern analysis technique including sensing a pressure envelope and monitoring the envelope pattern to locate characteristic changes and thereby identify systolic and diastolic pressures. The method further includes comparing the parameters measured using the distinct measurement techniques, determining mutually consistent limits for the distinct measurement techniques, and rejecting measurement samples outside the determined limits. Results produced by the distinct measurement techniques are combined to quantify an optimal systolic pressure result and an optimal diastolic pressure result.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENTS

Figure 1:
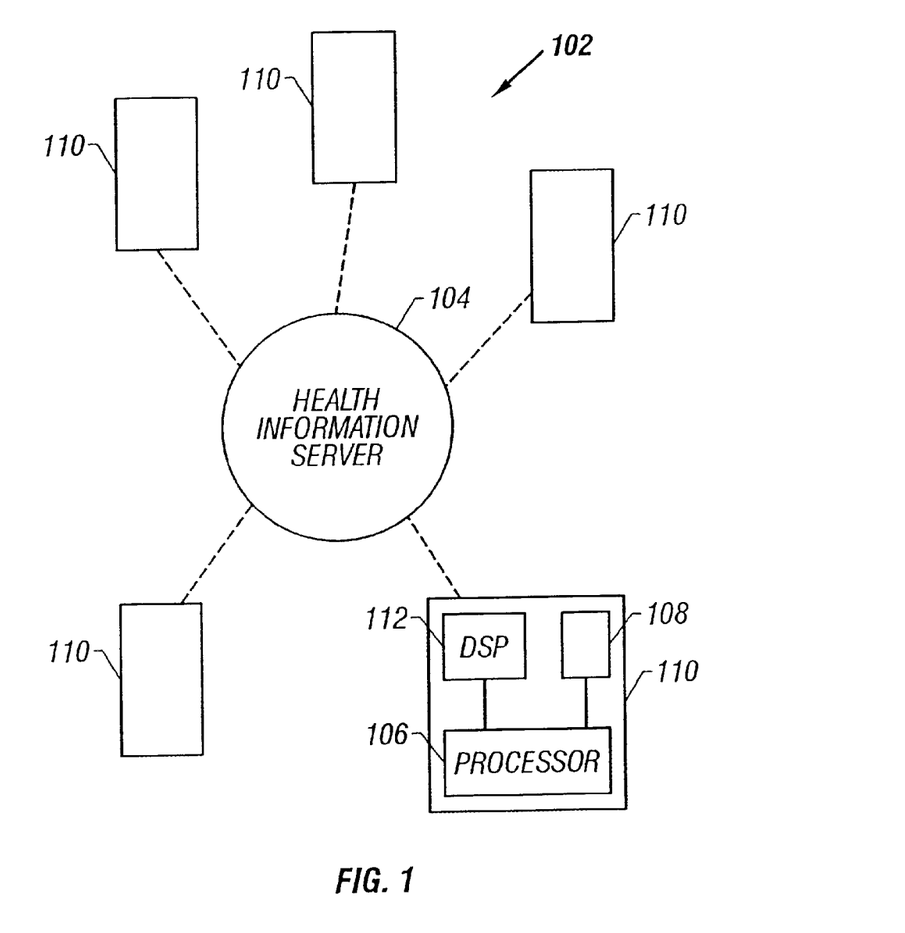
FIG. 1 is a schematic block diagram illustrating a suitable network for interconnecting one or more health information kiosks and a health information server.

Referring to FIG. 1, a schematic block diagram illustrates a suitable network 102 for interconnecting one or more health information kiosks 110 and a health information server 104. Typically, an individual health information kiosk 110 includes a processor 106 or controller with a storage 108 or memory that maintains a local archive of user information that stores a relatively small number of relatively recent test results, measurements, and possibly other information. The processor 106 executes a logic (not shown), typically a computer program, that is stored as software, firmware, control logic or other executable forms as are known by one of ordinary skill in the art. In an illustrative health care information system 100, the health information kiosk 110 employs additional computing power by adding a digital signal processor (DSP) 112 that operates in conjunction with the processor 106 to perform computation-intensive operations such as various health test operations.

The local archive includes tracking of health reading including blood pressure, heart rate and weight. Individual users also have an individual personal health site on the health information server 104. The health information server 104 is generally used to store a long-term archive of user results, measurements, and information received from the individual health information kiosks 110. In one example, the local health information kiosk 110 stores information from many users and all information that is generated on the health information kiosk 110 is automatically loaded, for example on a daily basis, to the central health information server 104. The results are sent to the health information server 104 for long-term storage and archiving. The information for the individual users are stored on corresponding personal health sites that are assigned to the particular individual users so that accurate and current information are available for all of the individual users.

In the illustrative example, the individual users determine the degree and level of health care information to be acquired and stored on the site. The individual user assigns a privilege level to allow the user's physician or pharmacist to enter information to the site with a desired level of security. The physician or pharmacist having the privilege granted by the individual user gains entry to the user site upon entry of a physician or pharmacist license or registration number granted by a federal, state, or local licensing authority. Entry of the licensing or registration number enforces user security and privacy concerns, preventing fraudulent change to the user database. Using the secured access to the user's site, the physician can be allowed to download health care information to the user site. Information is not changed on the site so the physician's level of security insures accuracy of the downloaded information. The physician's security specification permits the physician to transmit secured prescription orders and records to the individual health care site.

The health care information system 100 benefits the individual users by permitting secured accessibility of health care information and prescription needs anywhere in the world through usage of the internet. The health care information system 100 supplies accurate and current individual health care information that is accessible in a crisis or emergency situation.

In one example, the health information server 104 includes a layered security program for protecting user data from privacy violations. In an example of a layered security program, a user's personal health site can have a sixteen digit security card for entry into the health information kiosk 110 and an individual personal identification (PID) number to access the user's personal health site on the health information server 104. The level of security is equivalent to the security of an ATM machine in which the only person having access is the user since the user establishes the PID number.

The health information kiosks 110 are generally accessible to the public. For example, pharmacies or drug stores are suitable facilities for supplying floor space for a health information kiosk 110. Other suitable facilities include other retail outlets, health care providers such as physician offices, clinics, hospitals, and the like. The facilities housing a health information kiosk 110 typically have an agreement with the kiosk supplier to supply information, services, and products. The health information kiosk 110 executes various functions such as health testing and health evaluation. In some systems, the health information kiosk 110 supports operations including health testing and measurement, health and fitness evaluation, and various health care information sources. Various health tests may be supported. Common health tests include blood pressure testing, heart rate testing, and the like. For example, some systems may support various noninvasive blood analyses using pulse oximetry data acquisition. Measurements may include simple or complex measurements. One common measurement is a weight measurement that is supplied using a seat scale that is installed into the seat of the health information kiosk 110. Health care information sources may include a medication encyclopedia, a vitamin and supplement encyclopedia, an electronic health care library, health care provider directories, and the like.

The health information kiosk 110 interfaces to a server such as a store computer system or to a centralized server that services a wide geographical area. For example, the health information kiosk 110 may interface to a local pharmacy or drug store computer. The health information kiosk 110 may alternatively interface to a main frame health information server 104 that services a large area such as a country or region of the world. The health information kiosk 110 in combination with the health information server 104 typically includes a highly comprehensive pharmacy library covering prescription medications and over-the-counter remedies.

The individual health information kiosks 110 commonly include display software that displays a selected idle presentation, an attract screen with still-frame or dynamic graphics, or plays video clips that promote a selected party such as the sponsoring store or medical service providers.

Software programs in the individual health information kiosks 110 is updated by downloading, for example via internet access, or media transfer such as removable disk loading.

The health information server 104 commonly supports Internet sites for user access of health information, storage of personal history information, and to shop for products that are not available local to the health information kiosk 110.

Figure 2:
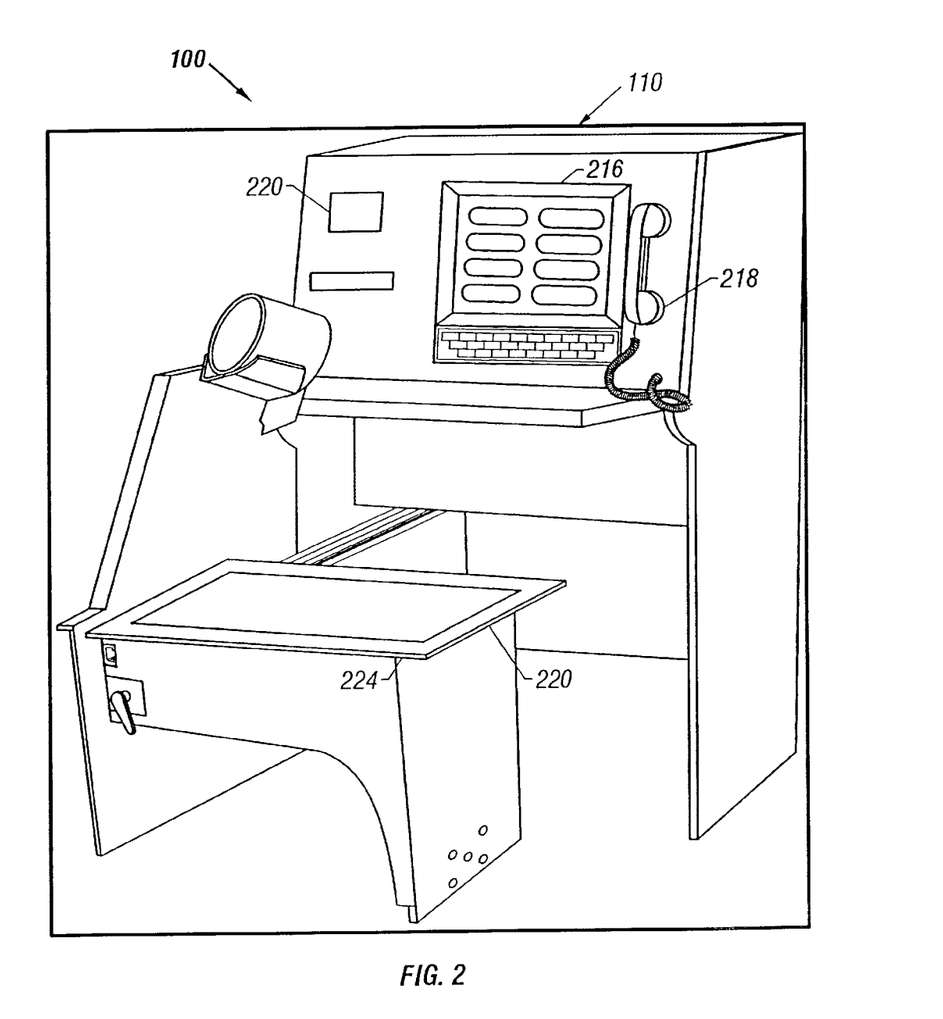
FIG. 2 is a pictorial diagram illustrating a suitable health information kiosk for usage in interfacing to a health care information system.
Figure 3:
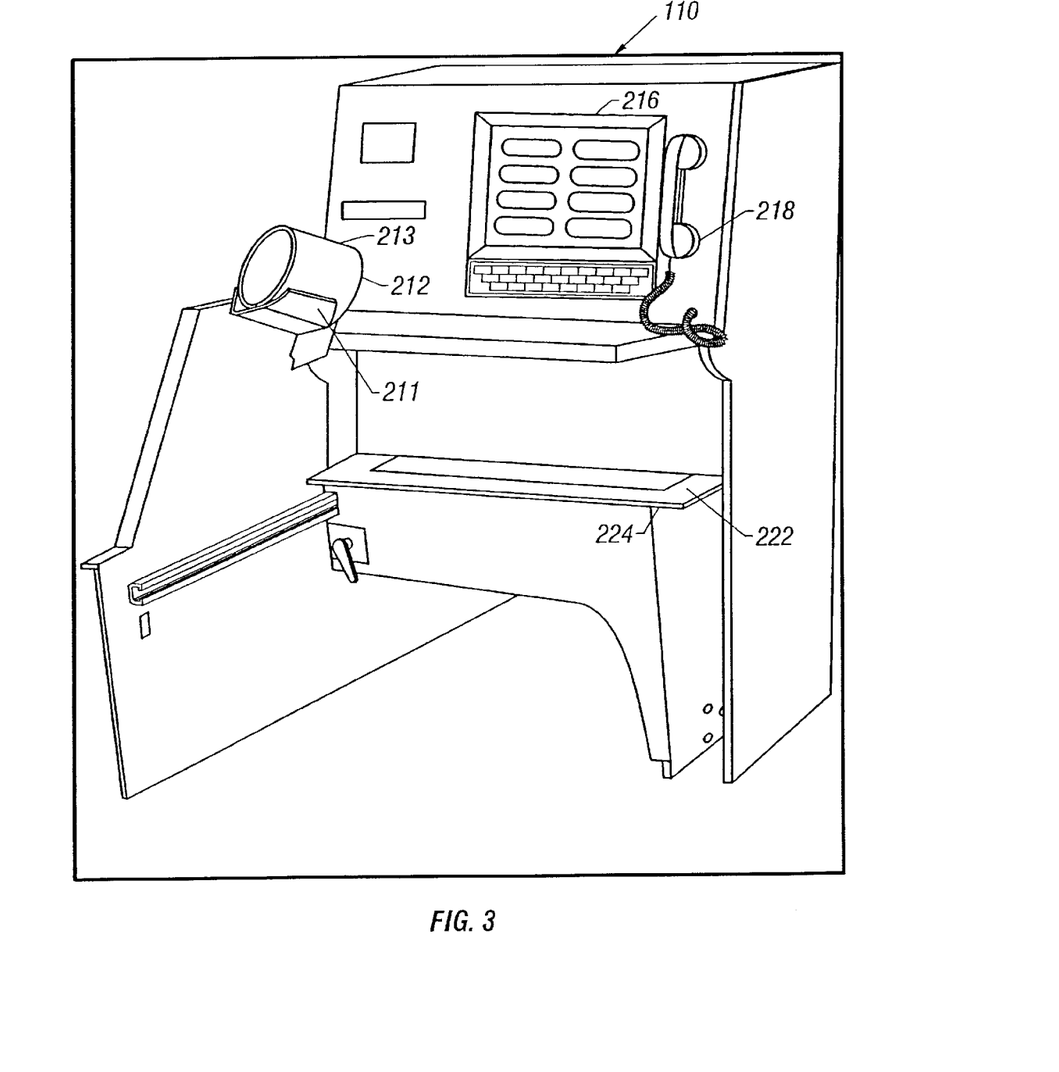
FIG. 3 is a pictorial diagram illustrating another view of the suitable health information kiosk with improved visualization of a blood pressure cuff.

Referring to FIGS. 2 and 3, a pictorial diagram shows a suitable health information kiosk 110 for usage in interfacing to a health care information system 100. The health information kiosk 110 includes a test interface 212 and a display 216. The display 216 can be configured as a touch-screen user input interface such as a touch-screen keyboard for operation as an input device. Some examples of the health information kiosk 110 can include a measurement interface 222 such as a weighing scale. The test interface 212 and display 216 are connected to a processor or controller (not shown) that executes diagnostic test operations using data acquired using the test interface 212. In an illustrative example, the test interface 212 is a blood pressure cuff 213 for acquiring blood pressure measurements. A microphone 211 is attached to the blood pressure cuff 213 to measure a sound or audio signal. The touch screen display 216 in the configuration as a user interface or keyboard is used to acquire patient data and other information from the user. The processor includes communication interfaces for communicating with the test interface 212, the display 216, and a remote terminal so that the health information kiosk 110 can be connected into a communication network (not shown). In some systems, the health care information system 100 includes a telephone handset 218 that a user may employ to receive information from the health care information system 100 in privacy or for usage in telephone communication. Some versions of the health information kiosk 110 optionally include a printer 220 for printing test results, information materials, advertisements, coupons, and the like.

The illustrative test interface 212 is a blood pressure cuff 213 with one or more pressure transducers (not shown) for acquiring blood pressure waveforms from the user. The pressure transducer has an electrical connection to the processor via the communication interface so that pressure waveform data is supplied to the processor. The processor executes a computerized blood pressure detection algorithm to produce highly accurate measurements of systolic and diastolic blood pressure, and mean blood pressure. The processor also analyzes the blood pressure waveforms to detect heart rate information.

The processor executes software programs including data analysis routines that produce highly accurate blood pressure and heart rate measurements. The health care information system 100 acquires other health care information from the patient and from various health care databases via network communication linkages to generate a full health appraisal. The health care information system 100 includes local storage and the network communication link to external storage resources to allow a user to access pertinent health care information. For example, the health care information system 100 permits the user to access a full medication encyclopedia that lists pharmaceutical medications that are currently available on the market. A health care provider directory is accessible via the network interconnection, either on the kiosk or by an Internet connection, to enable the user to find area physicians, specialists, clinics, hospitals, health maintenance organizations (HMOs), and the like.

One example of a suitable display 216 is a high-resolution Active Matrix color touchscreen display. The display 216 is used to present menus and controls, as well as to present information including test results, measurements, health information such as seasonal health information. A text display shows text in one or more of various selected languages. Many other displays of various sizes, specifications, and utilizing various technologies are also suitable.

One example of a suitable test interface 212 is a blood pressure cuff 213 including a nylon washable exterior cuff with a seamless inner natural latex bladder that is inflated using a pneumatic power system. A suitable cuff size is 30×12.5 cm. The cuff can be constructed of medical grade silicone tubing that is non-reactive, and thus allergy-free, to body tissue. Cuff pressure is regulated by pressure monitors (not shown) that are inherently stable and are calibrated to function accurately with cuff pressure variations of less than +/−1% over a full operating range of systolic maximum pressure 250 mm-Hg and minimum pressure 80mm-Hg, and diastolic maximum pressure 130mm-Hg and minimum pressure 38mm-Hg, a differentiation of 8 points between systolic and diastolic pressure, and a heart rate from 38 to 200 bpm. The monitors use automatic zero pressure variations to prevent accuracy from being affected by altitude level or other changes in atmospheric pressure, temperature, and humidity. The exemplary test interface 212 also detects sound signals for usage with Korotkoff sound detection. Both pressure signals and sound signals are converted to digital form and transmitted to the processor to perform blood pressure measurements using both oscillometric and auscultatory analysis. The pressure and sound signals can be processed to determine heart rate measurement using a beat-to-beat averaging method. In some examples, tests are activated using a touch screen in which a virtual green start button initiates a test procedure by inflating the cuff positioned about the patient's arm. Touching the display screen halts the test and returns the pneumatic cuff to the open position. Various other specifications, materials, and technologies or combinations of technologies that are known by those having ordinary skill in the art are also suitable.

An illustrative measurement interface 222 is a weighing scale formed into a moveable seat 224 that is attached to the health information kiosk 110. The seat scale has accuracy within one pound. In some systems, the seat 224 of the health information kiosk 110 is moveable so that the test interface 212 and display 216 are wheel-chair accessible and easily used by the disabled without assistance.

Figure 4:
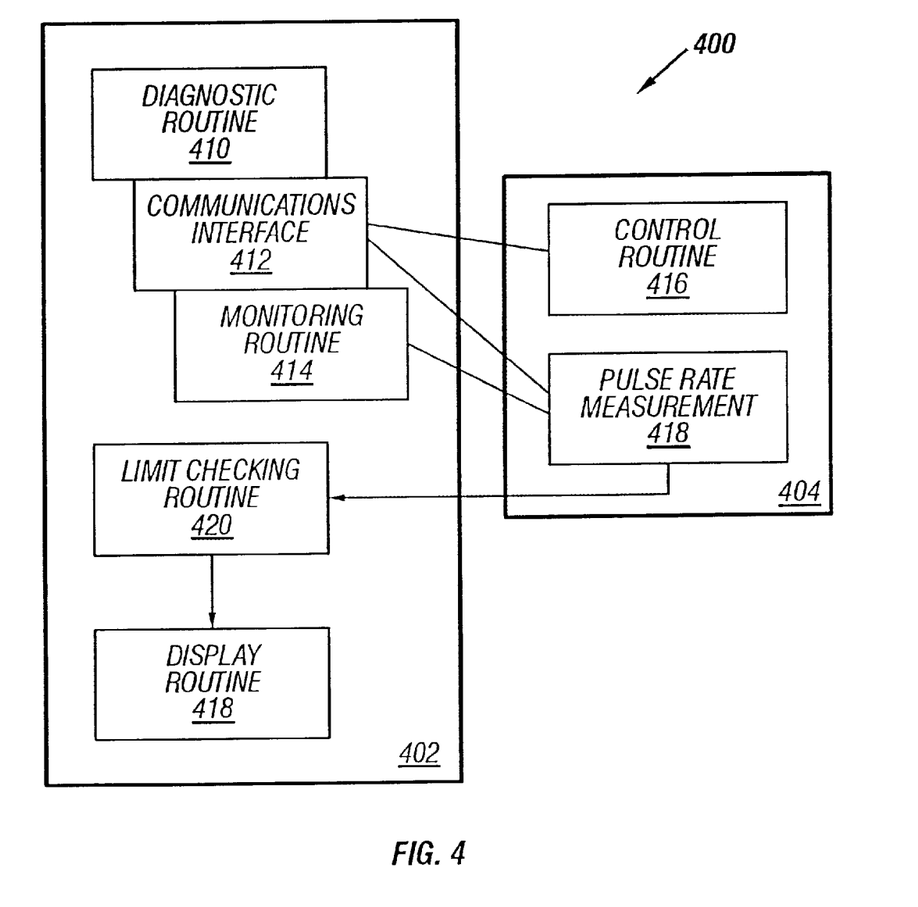
FIG. 4 is a schematic block diagram showing functional elements of a blood pressure measurement operation that can be performed by the health care information system.

Referring to FIG. 4, a schematic block diagram shows functional elements of a blood pressure measurement operation that can be performed by the health care information system. In an illustrative embodiment, a blood pressure measurement routine 400 is implemented for usage on the digital signal processor 112 that operates in combination with control operations executed on the processor 106. One suitable digital signal processor 112 is a 32-bit floating-point processor. Basis operating routines in the blood pressure measurement routine 400 that can be functionally divided into operating system functions 402 and measurement operations 404. The operating system functions 402 include a basic integrity diagnostic routine 410, a communications interface 412, and a monitoring routine 414 for monitoring switch input signals and sensor data. The measurement operations 404 include a control routine 416 that controls cuff inflation and bleed cycles and a pulse rate measurement routine 418 to compute the blood pressure result. The measurement operations 404 return processing control back to the operating functions 402 to execute a limit checking routine 420 and a display routine 422 for displaying individual blood pressure measurements, or values associated with a combination of measurement values.

Figure 5:
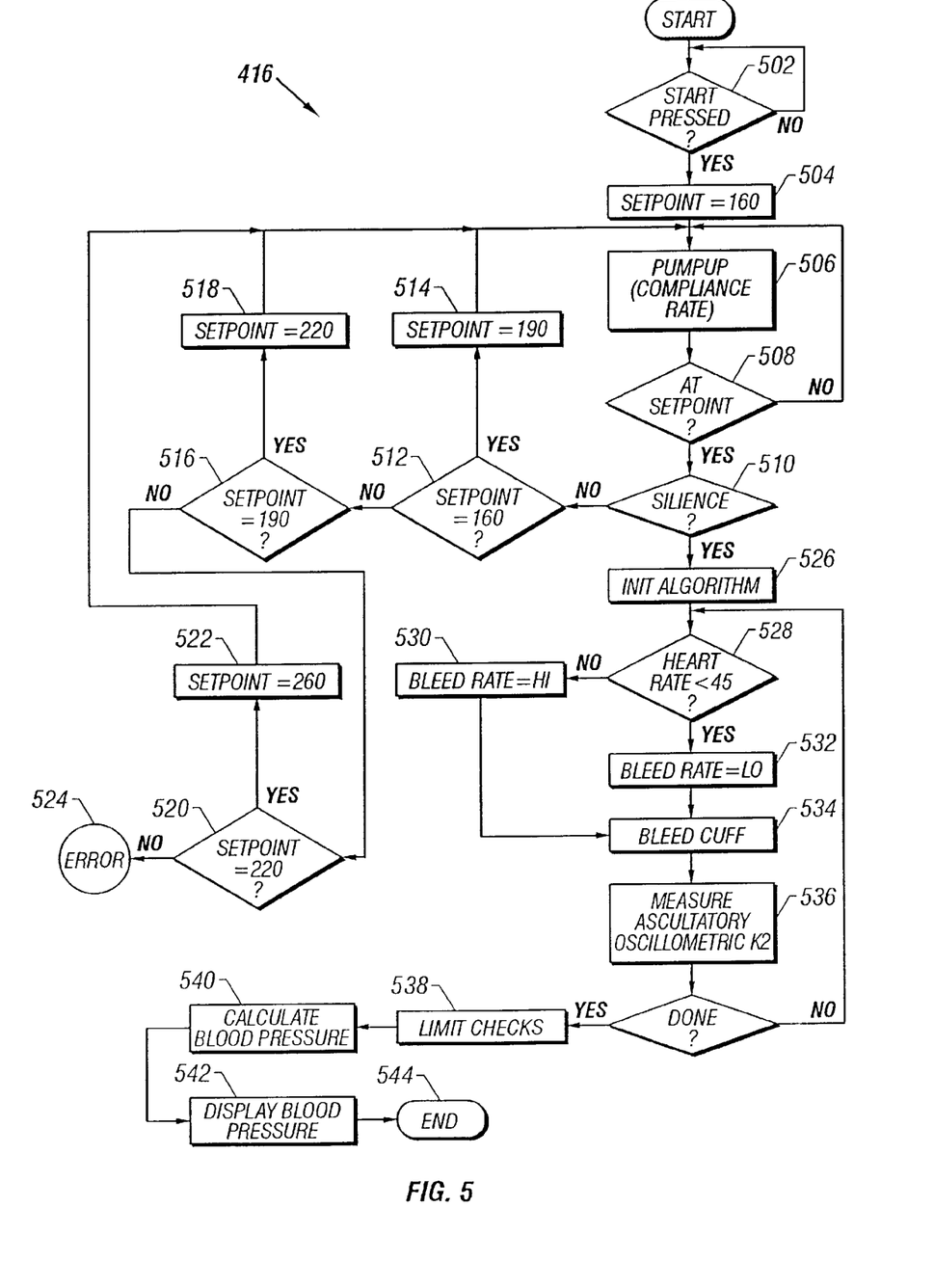
FIG. 5 is a schematic flow chart that depicts a suitable control routine for controlling the blood pressure measurement.

Referring to FIG. 5, a schematic flow chart depicts suitable measurement operations 404 including the control routine 416 for controlling the blood pressure measurement. The control routine 416 inflates the blood pressure cuff 213 shown in FIG. 2. The user presses a START button 502 on the health information kiosk 110, sending a signal to the processor 106 to begin inflating the blood pressure cuff 213. The control routine 416 initializes a pressure setpoint 504 to a common level of 160 mm-Hg and starts a Pump-up cycle 506 that inflates the cuff bladder to the initial pressure setpoint. During the Pump-up cycle 506, the pressure is increased at a controlled rate to avoid blood vessel compliance issues that could reduce measurement accuracy. Four pumping levels are used to attain a reduced or minimal pumping pressure level, thus reducing the noise level during detection of Korotkoff sounds. For example, if the Pump-up cycle 506 increases the pressure to 160 mm-Hg as determined by a pressure limit test 508 and an audio test for Korotkoff sounds 510 does not sense a "silent" level, then the setpoint is first increased to 190 mm-Hg 514 and the Pump-up cycle 506 gradually increases the pressure to 190 mm-Hg. If the absence of Korotkoff sounds is not detected in function block 510 at pressures of 160 mm-Hg and 190 mm-Hg, the setpoint is set and tested for setpoints of 220 mmHg and 260 mm-Hg in function blocks 518 and 522, respectively, as controlled by logic operations in blocks 512, 516, and 520. If Korotkoff sounds are not eliminated even at a pressure of 260 mm-Hg, then the test is aborted and an error message is generated in block 524.

When the pressure is set to the setpoint, as determined by the cessation of Korotkoff sounds in block 510, then a measurement initialization operation 526 initializes the blood pressure measurement parameters. A bleed rate is selected that is either a high bleed rate in operation 530 or a low bleed rate 532, depending on the user's heart or pulse rate, as determined by logic operation 528.

During a cuff bleed cycle 534, the blood pressure measurement routine 400 gradually reduces pressure in the cuff 213 while executing three separate analysis operations 536 that analyze sampled data. In the illustrative blood pressure measurement routine 400, the three test techniques including an ascultatory technique, an oscillometric technique, and a pattern recognition technique. In some systems, the three analysis operations are executed sequentially. In other systems, the analysis operations can execute simultaneously or concurrently. For example, some systems may include multiple processors or may use multi-threading, multi-processing or superscalar processing techniques and the like to attain computational efficiencies.

The blood pressure measurement routine 400 supplies results from the three separate analysis techniques to an operating system 502 executing in the processor 106 which executes a limit checking operation 538, a blood pressure calculation operation 540, a display operation 542, and an end operation 544.

Figure 6:
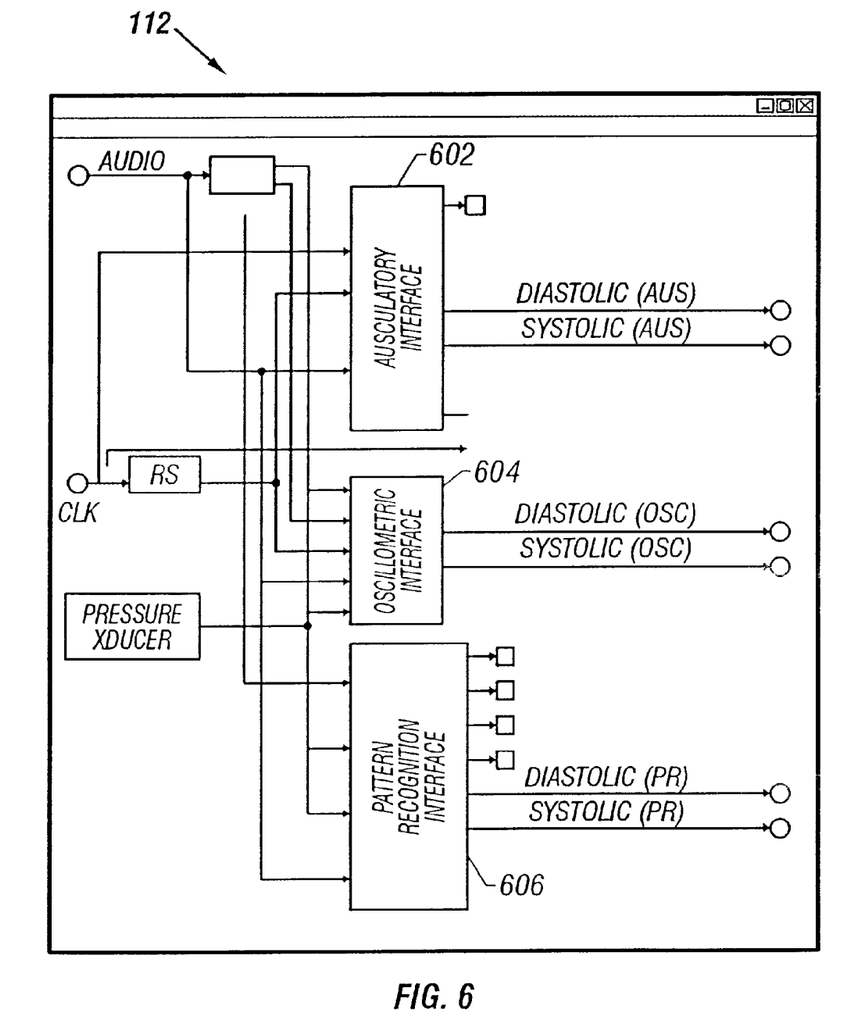
FIG. 6 is a schematic block diagram that illustrates a test interface that is suitable for performing multiple analysis operations.

The multiple separate analysis operations 536 are performed by the test interface 112 depicted in a block diagram shown in FIG. 6 in which an ascultatory interface 602, an oscillometric interface 604, and a pattern recognition interface 606 function in combination to improve the accuracy of a blood pressure measurement. The ascultatory interface 602 functions as a controlling measurement that determines diastolic and systolic pressure points from audio signals. The diastolic and systolic pressure points that are determined using the ascultatory technique 602 are used to define the sequence of the measurement cycle for the oscillometric technique 604 and the pattern recognition technique 606. The measurement using the oscillometric technique 604 uses oscillations on a measured pressure waveform to locate systolic and diastolic pressures. The pattern recognition technique 606 employs pattern recognition to locate characteristic changes in the sound envelope to determine systolic and diastolic pressures.

Figure 7:
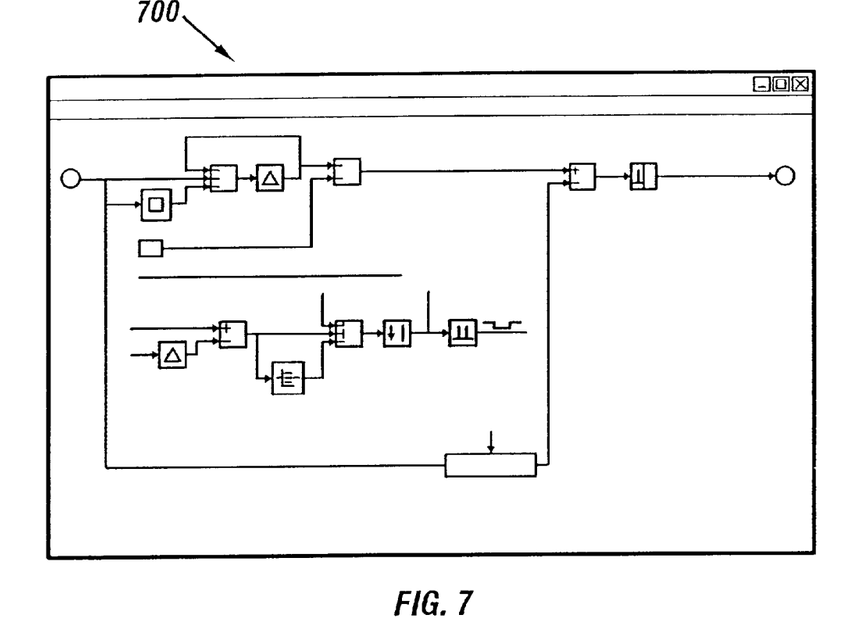
FIG. 7 is a schematic block diagram showing a pulse discriminator for extracting a user pulse signal directly from an output terminal of a pressure transducer attached to a pressure cuff.

Input signals to the test interface 112 include a sound signal from the microphone 211 located in the pressure cuff 213, and a pressure signal which indicates cuff pressure. A pulse discriminator 700 shown in FIG. 7 extracts the user pulse signal directly from an output terminal of a pressure transducer (not shown) attached to the pressure cuff 213. The pulse discriminator 700 extracts the user's pulse signal directly from the pressure signal produced by the pressure transducer. The pulse discriminator detects a pulse by monitoring variations in the pressure signal including the slope and the rate of change of the slope of the pressure signal.

Figure 8:
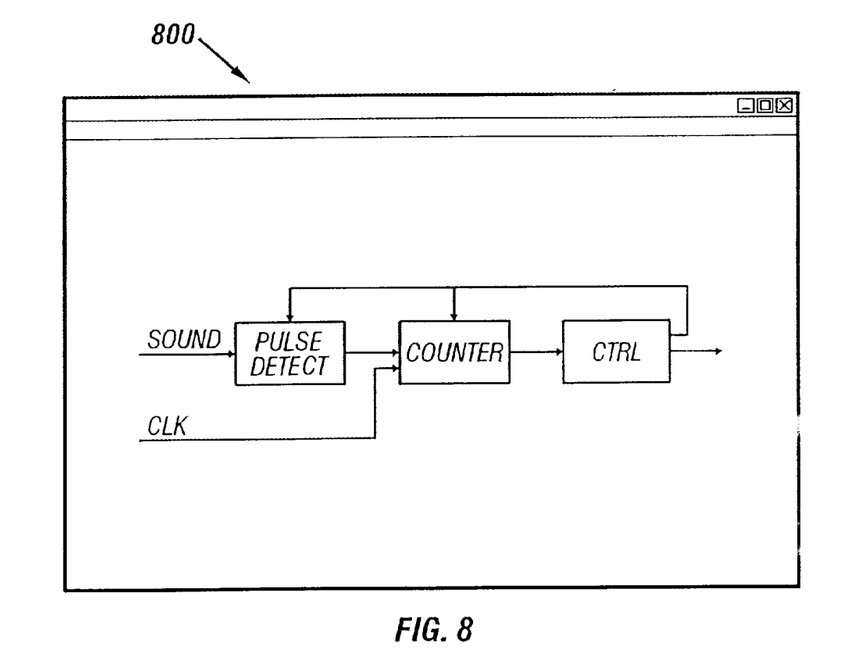
FIG. 8 is a schematic block diagram illustrating a measurement cycle controller that generates signals governing a measurement cycle based on sensed sound signals.

Referring to FIG. 8, a schematic block diagram illustrates a measurement cycle controller 800 that generates signals governing a measurement cycle based on sensed sound signals. Korotkoff sounds detected from the microphone 211 in the pressure cuff 213 control the measurement cycle. The measurement cycle controller 800 initially waits for first sounds. When the measurement cycle controller 800 detects the first sounds, a cycle begins. The measurement cycle controller 800 detects subsequent sounds and times the duration between sounds. When the duration between Korotkoff sounds is more than a selected duration, the measurement cycle controller 800 registers that a period of silence has occurred, which ends the measurement cycle.

Figure 9:
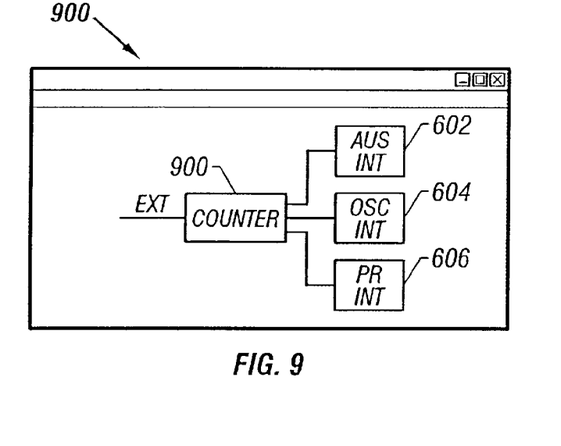
FIG. 9 is a schematic block diagram that shows a sample counter that generates a sample count for marking event times.

Referring to FIG. 9, a schematic block diagram shows a sample counter 900 that generates a sample count for marking event times. The sample counter 900 is synchronized by an external signal and maintains a sample count that is used by each of the ascultatory interface 602, the oscillometric interface 604, and the pattern recognition interface 606 to mark event times. The sample counter 900 marks the systolic and diastolic events for external displays.

Figure 10:
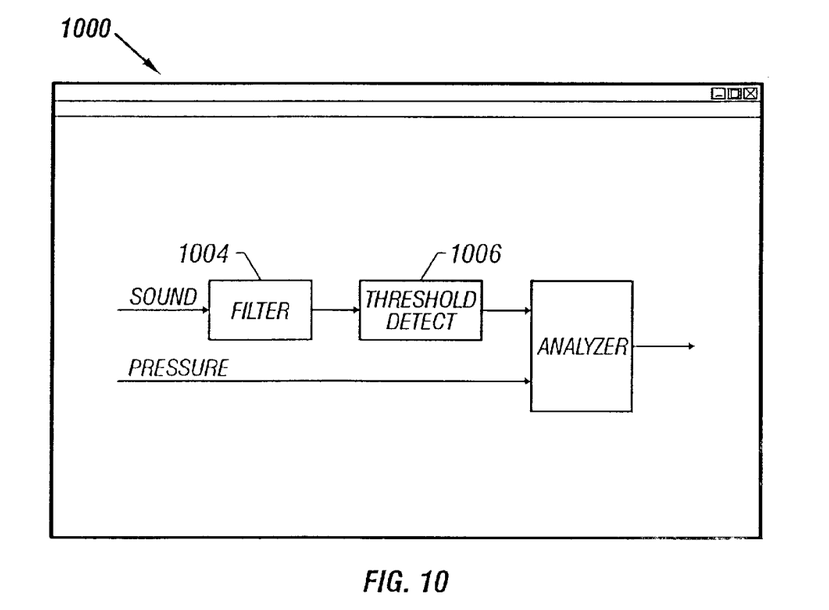
FIG. 10 is a schematic block diagram that shows an example of a suitable ascultatory interface for measuring blood pressure using an ascultatory technique.

Referring to FIG. 10, a schematic block diagram shows an example of a suitable ascultatory interface 602 for measuring blood pressure using the ascultatory technique 602. The ascultatory technique 602 determines systolic and diastolic pressures by using a microphone and signal processing to detect an onset of Korotkoff sounds and a lapse of Korotkoff sounds. The ascultatory technique 602 is similar to the manual technique that is conventionally used by health care practitioners. The ascultatory interface 602 detects and stores the systolic and diastolic pressures. The ascultatory interface 602 has an input terminal that connects to the microphone 211, a filter 604, and a threshold detector 606. The filter 604 has filter characteristics that are similar to the characteristics of a stethoscope and operates by sorting sound components that are characteristic of the Korotkoff sounds. The threshold detector 606 detects the presence or absence of the Korotkoff sounds. To avoid false detection, the ascultatory interface 602 employs sequential analysis techniques to detect false conditions.

The techniques for detecting Korotkoff sounds are well known the health care practitioners having ordinary skill in the art. The ascultatory interface 602 implements the well known manual ascultatory techniques using computer hardware and software techniques that are well known to those having ordinary skill in the computer arts.

Figure 11:
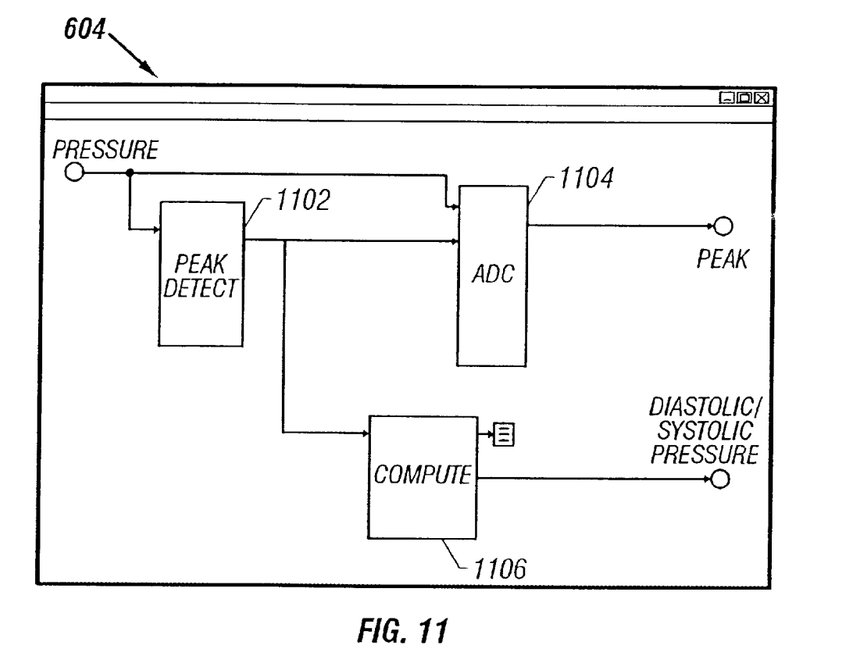
FIG. 11 is a schematic block diagram that shows an example of a suitable oscillometric interface for measuring blood pressure using an oscillometric technique.

Referring to FIG. 11, a schematic block diagram shows an example of a suitable oscillometric interface 1100 for measuring blood pressure using an oscillometric technique. The oscillometric interface 604 has an input terminal that is connected to the pressure cuff 213 and receives the pressure signal. The oscillometric interface 604 monitors the pressure oscillations in the pressure cuff 213. The oscillometric interface 604 includes a peak detector 1102, an analog-to-digital converter 1104, and a computation block 1106. For a pulse, the oscillometric interface 604 detects the peak pressure using the peak detector 1102, determines the amplitude of the pressure at the peak by sampling the pressure signal waveform using the analog-to-digital converter 1104. The oscillometric interface 604 saves the sampled peak amplitude. The computation block 1106 averages the pressure measurements throughout the pulse cycle. Upon determination of the mean pressure, the computation block 1106 uses an empirical systolic ratio to find the systolic pressure pulse and associated cuff pressure. The computation block 1106 then uses the diastolic pressure to subsequently find the diastolic pulse and the cuff pressure associated with the diastolic pulse. Both systolic and diastolic measurement techniques employ heuristic filtering techniques to ignore known pressure pulse events that would otherwise produce erroneous results.

Figure 12:
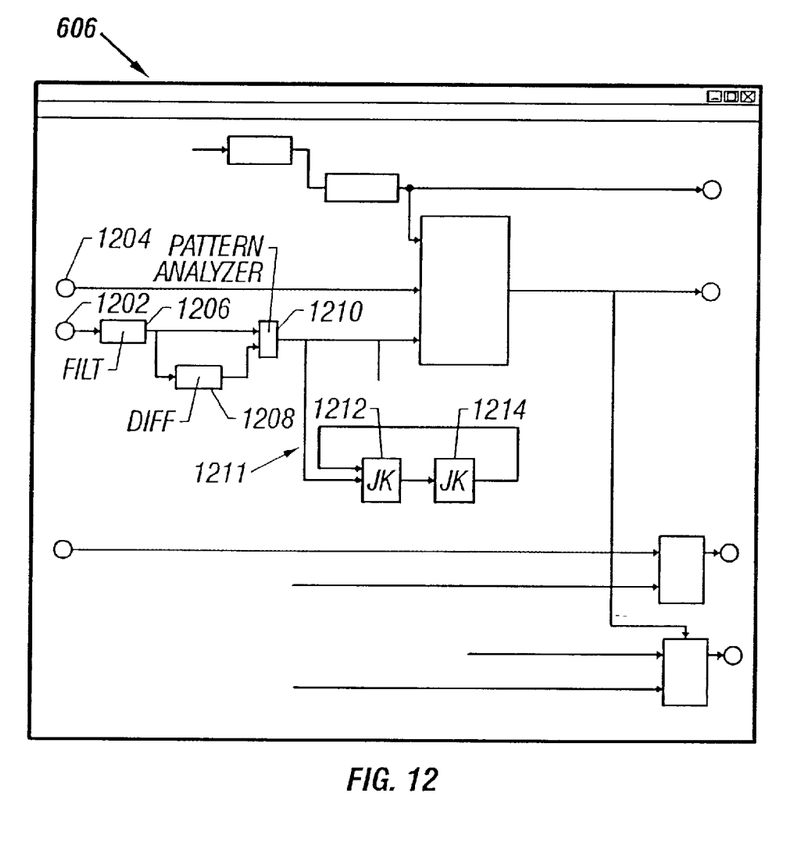
FIG. 12 is a schematic block diagram that shows an example of a suitable pattern recognition interface for measuring blood pressure using a pattern recognition technique.

Referring to FIG. 12, a schematic block diagram shows an example of a suitable pattern recognition interface 606 for measuring blood pressure using a pattern recognition technique. The pattern recognition interface 606 includes a first input terminal 1202 that is connected to the microphone 211 and a second input terminal 1204 that is connected to the pressure cuff 213. The first input terminal 1202 is connected to a smoothing filter 1206, a differentiator 1208, pattern analyzer 1210, and glitch logic 1211. The pattern recognition interface 606 searches for a pattern recognition signature by first smoothing the audio signal from the distal microphone 211 using the smoothing filter 1206, and using the differentiator 1208 to determine the second derivative of the audio signal, thereby magnifying a residual noise component of the audio signal. To affirm that a valid pattern recognition signature is found, the pattern analyzer 1210 searches for a characteristic asymmetric "W" pattern during the pulse interval. The negative edge of the pulse signal is delayed with the duration of the delay being indicative of validity and invalidity of the systolic pattern. The glitch logic 1211 includes J-K flip-flops 1212 and 1214 and is used to eliminate spurious match signals to verify that two consecutive match signals exist. The first J-K flipflop 1212 latches the systolic pressure and sample count. The second J-K flip-flop 1214 latches the pressure and sample count for the last match that occurs. The diastolic pressure and sample count are updated for every match and correspondingly latch the pressure and sample count for the last match that occurs.

The pattern recognition interface 606 and technique use pattern recognition to determine sound signal characteristics that are highly correlated to intra-arterial measurements of systolic and diastolic blood pressure.

The multiple facets of the illustrative blood pressure measurement, including the ascultatory interface 602, the oscillometric interface 604, and the pattern recognition interface 606, assure accuracy. Results of the three separate measurements are checked against a set of predetermined limit values and compared. The resulting numbers are used to calculate a mean systolic pressure and a mean diastolic pressure.

The test interface 112 uses digital signal processor technology to implement a multiple-method measurement technique. The test interface 112 uses the digital signal processor to simultaneously execute separate measurements in real time, but at a low cost, to permit a choice of the optimum measurement result. Furthermore, usage of the digital signal processor employs processing of digital signals rather than analog signal processing. Analog signal processing results in errors and spurious variation in measurement results due to variations in environmental conditions. In contrast, digital signal processing is generally immune to environmental variations.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A test apparatus comprising:
   an ascultatory analyzer that is capable of sensing and analyzing an audio signal using Korotkoff sounds to determine a systolic pressure and a diastolic pressure;
   an oscillometric analyzer that is capable of sensing and analyzing oscillations of a pressure signal to determine the systolic pressure and the diastolic pressure, the oscillometric analyzer using information from the ausculatory analyzer to sense and analyze the oscillations;
   a pattern recognition analyzer that is capable of sensing a pressure envelope and analyzes the pressure envelope using a pattern recognition analysis by monitoring the envelope pattern to locate characteristic changes, and identifying systolic and diastolic pressures from the characteristic changes; and
   a control element coupled to the ascultatory analyzer, the oscillometric analyzer, and the pattern recognition analyzer that determines an optimal systolic pressure result and an optimal diastolic pressure result based on results from the ascultatory analysis, the oscillometric analysis and the pattern recognition analysis.

2. A test apparatus comprising:
   an ascultatory analyzer that is capable of sensing and analyzing an audio signal using Korotkoff sounds to determine a systolic pressure and a diastolic pressure;
   an oscillometric analyzer that is capable of sensing and analyzing oscillations of a pressure signal to determine the systolic pressure and the diastolic pressure;
   a pattern recognition analyzer that is capable of sensing a pressure envelope and analyzes the pressure envelope using a pattern recognition analysis by monitoring the envelope pattern to locate characteristic changes, and identifying systolic and diastolic pressures from the characteristic changes;
   a comparison block coupled to the ascultatory analyzer, the oscillometric analyzer, and the pattern recognition analyzer that determines an optimal systolic pressure result and an optimal diastolic pressure result based on results from the ascultatory analysis, the oscillometric analysis and the pattern recognition analysis; and
   a pulse discriminator that is capable of sensing and analyzing an audio signal including determining an audio signal slope and slope rate of change, the pulse discriminator generating a pulse signal that is used by one or more of the ascultatory analyzer, the oscillometric analyzer, and the pattern recognition analyzer to define a measurement cycle that is used for analysis.

3. A test apparatus according to claim 1 further comprising:
   a measurement cycle controller that is capable of sensing and analyzing an audio signal using Korotkoff sounds to determine a measurement cycle start at a first Korotkoff sound and a measurement cycle end at a cessation of Korotkoff sounds.

4. A test apparatus according to claim 1 wherein:
   the ascultatory analyzer includes a filter that sorts sound components of Korotkoff sounds.

5. A test apparatus according to claim 1 wherein:
   the oscillometric analyzer senses a pressure pulse height, determines a mean pressure and an empirical systolic ratio to find a systolic pressure pulse and associated systolic pulse cuff pressure, and determines a mean pressure and an empirical diastolic ratio to find a diastolic pressure pulse and associated diastolic pulse cuff pressure.

6. A test apparatus according to claim 1 wherein the pattern recognition analyzer further includes:
   an input terminal that is capable of being coupled to a microphone for detecting an audio signal;
   a filter coupled to the input terminal that smoothes the audio signal;
   a differentiator that magnifies a residual noise component of the audio signal; and
   a pattern analyzer that detects an asymmetric "W" pattern during a pulse interval.

7. A test apparatus according to claim 1 wherein the pattern recognition analyzer further includes:
   an input terminal that is capable of being coupled to a microphone for detecting an audio signal;
   a first latch that latches a systolic pressure and sample count; and
   a second latch that latches a diastolic pressure and sample count.

8. A test apparatus according to claim 1 further comprising:
   a blood pressure cuff;
   a pressure pump coupled to the blood pressure cuff; and
   a controller coupled to the pressure pump for controlling pressure in the blood pressure cuff.

9. A test apparatus according to claim 1 further comprising:
a microphone for sensing the audio signal.

10. A blood pressure measurement system comprising:
a kiosk;
a blood pressure interface coupled to the kiosk and capable of detecting a pressure signal;
a microphone coupled to the blood pressure interface and capable of detecting an audio signal; and
a blood pressure analyzer coupled to the kiosk, the blood pressure interface, and the microphone, the blood pressure analyzer including a plurality of separate analyzers that detect blood pressure using a plurality of separate analysis techniques, the plurality of analysis techniques being based on audio signals, on pressure oscillations, and on a pattern recognition, information being shared for performance of the audio signal and pattern recognition analysis techniques.

11. A blood pressure measurement system comprising:
a kiosk;
a blood pressure interface coupled to the kiosk and capable of detecting a pressure signal;
a microphone coupled to the blood pressure interface and capable of detecting an audio signal; and
a blood pressure analyzer coupled to the kiosk, the blood pressure interface, and the microphone, the blood pressure analyzer including a plurality of separate analyzers that detect blood pressure using a plurality of separate analysis techniques, the plurality of analysis techniques being based on audio signals, on pressure oscillations, and on a pressure envelope, information from the separated analyzers being shared for performance of the analysis techniques; wherein the plurality of separate analyzers comprise:
   an ascultatory analyzer that is capable of sensing and analyzing the audio signal using Korotkoff sounds to determine a systolic pressure and a diastolic pressure;
   an oscillometric analyzer that is capable of sensing and analyzing oscillations of a pressure signal to determine the systolic pressure and the diastolic pressure, the oscillometric analyzer using information from the ascultatory analyzer to sense and analyze the oscillations; and
   a pattern recognition analyzer that is capable of sensing a pressure envelope and analyzes the pressure envelope using a pattern recognition analysis by monitoring the envelope pattern to locate characteristic changes, and identifying systolic and diastolic pressures from the characteristic changes; and
a control element coupled to the ascultatory analyzer, the oscillometric analyzer, and the pattern recognition analyzer that determines an optimal systolic pressure result and an optimal diastolic pressure result based on results from the ascultatory analysis, the oscillometric analysis and the pattern recognition analysis.

12. A blood pressure measurement system comprising
a kiosk;
a blood pressure interface coupled to the kiosk and capable of detecting a pressure signal;
a microphone coupled to the blood pressure interface and capable of detecting an audio signal;
a blood pressure analyzer coupled to the kiosk, the blood pressure interface, and the microphone, the blood pressure analyzer including a plurality of separate analyzers that detect blood pressure using a plurality of separate analysis techniques, the plurality of analysis techniques being based on audio signals, on pressure oscillations, and on a pressure envelope;
an ascultatory analyzer that is capable of sensing and analyzing the audio signal using Korotkoff sounds to determine a systolic pressure and a diastolic pressure;
an oscillometric analyzer that is capable of sensing and analyzing oscillations of a pressure signal to determine the systolic pressure and the diastolic pressure;
a pattern recognition analyzer that is capable of sensing a pressure envelope and analyzes the pressure envelope using a pattern recognition analysis by monitoring the envelope pattern to locate characteristic changes, and identifying systolic and diastolic pressures from the characteristic changes;
a comparison block coupled to the ascultatory analyzer, the oscillometric analyzer, and the pattern recognition analyzer that determines an optimal systolic pressure result and an optimal diastolic pressure result based on results from the ascultatory analysis, the oscillometric analysis and the pattern recognition analysis; and
a pulse discriminator that is capable of sensing and analyzing an audio signal including determining an audio signal slope and slope rate of change, the pulse discriminator generating a pulse signal that is by used one or more of the ascultatory analyzer, the oscillometric analyzer, and the pattern recognition analyzer to define a measurement cycle that is used for analysis.

13. A system according to claim 11 further comprising:
a measurement cycle controller that is capable of sensing and analyzing an audio signal using Korotkoff sounds to determine a measurement cycle start at a first Korotkoff sound and a measurement cycle end at a cessation of Korotkoff sounds.

14. A system according to claim 11 wherein:
the ascultatory analyzer includes a filter that sorts sound components of Korotkoff sounds.

15. A system according to claim 11 wherein:
the oscillometric analyzer that senses a pressure pulse height, determines a mean pressure and an empirical systolic ratio to find a systolic pressure pulse and associated systolic pulse cuff pressure, and determines a mean pressure and an empirical diastolic ratio to find a diastolic pressure pulse and associated diastolic pulse cuff pressure.

16. A system according to claim 11 wherein the pattern recognition analyzer further includes:
an input terminal that is capable of being coupled to a microphone for detecting an audio signal;
a filter coupled to the input terminal that smoothes the audio signal;
a differentiator that magnifies a residual noise component of the audio signal; and
a pattern analyzer that detects an asymmetric "W" pattern during a pulse interval.

17. A system according to claim 11 wherein the pattern recognition analyzer further includes:
an input terminal that is capable of being coupled to a microphone for detecting an audio signal;
a first latch that latches a systolic pressure and sample count; and
a second latch that latches a diastolic pressure and sample count.

18. A method of measuring blood pressure of a test subject comprising:

sensing an audio signal;

analyzing the audio signal using an ascultatory analysis of Korotkoff sounds to determine a systolic pressure and a diastolic pressure;

sensing pressure oscillations;

analyzing the pressure oscillations using an oscillometric analysis; further including:
  determining mean pressure, systolic and diastolic blood pressure from the pressure oscillations; and
  identifying systolic and diastolic pressures from the mean pressure, and systolic and diastolic blood pressure;

sensing a pressure envelope;

analyzing the pressure envelope using a pattern recognition analysis including:
  monitoring the envelope pattern to locate characteristic changes;
  identifying systolic and diastolic pressures from the characteristic changes;

determining an optimal systolic pressure result and an optimal diastolic pressure result based on results from the ascultatory analysis, the oscillometric analysis, and the pattern recognition analysis; and sharing information from the separate sensing actions among the separate analyzing actions.

19. A method according to claim 18 further comprising:

comparing the parameters measured using the distinct measurement techniques, determining mutually consistent limits for the distinct measurement techniques, and rejecting measurement samples outside the determined limits. Results produced by the distinct measurement techniques are combined to quantify an optimal systolic pressure result and an optimal diastolic pressure result.

20. A method according to claim 18 further comprising:

analyzing the audio signal including:
  determining an audio signal slope and slope rate of change;
  detecting a pulse based on the audio signal slope and slope rate of change; and
  generating a pulse signal that is by used one or more of the ascultatory analysis, the oscillometric analysis, and the pattern recognition analysis to define a measurement cycle.

21. A method according to claim 18 further comprising:

analyzing the audio signal using Korotkoff sounds to determine a measurement cycle start at a first Korotkoff sound and a measurement cycle end at a cessation of Korotkoff sounds.

22. A method according to claim 18 further comprising:

filtering the audio signal;

sorting sound components of Korotkoff sounds in the audio signal.

23. A method according to claim 18 further comprising:

sensing a pressure pulse height;

determining a mean pressure and an empirical systolic ratio to find a systolic pressure pulse and associated systolic pulse cuff pressure, and determining a mean pressure and an empirical diastolic ratio to find a diastolic pressure pulse and associated diastolic pulse cuff pressure.

24. A method according to claim 18 further comprising:

detecting an audio signal;

filtering the detected audio signal;

differentiating the audio signal to magnify a residual noise component of the audio signal; and detecting asymmetric "W" pattern during a pulse interval.

25. A method according to claim 18 wherein the pattern recognition analysis further includes:

detecting the audio signal;

latching a systolic pressure and sample count; and latching a diastolic pressure and sample count.

26. A method according to claim 18 further comprising:

inflating and deflating a blood pressure cuff; and controlling pressure in the blood pressure cuff.

27. A method according to claim 18 further comprising:

sensing the audio signal using a microphone.

28. A blood pressure measurement system comprising:

a kiosk;

a blood pressure interface coupled to the kiosk and capable of detecting a pressure signal;

a microphone coupled to the blood pressure interface and capable of detecting an audio signal; and a blood pressure analyzer coupled to the kiosk, the blood pressure interface, and the microphone, the blood pressure analyzer including a plurality of separate analyzers that detect blood pressure using at least three separate analysis techniques, the analysis techniques being based on audio signals, on pressure oscillations, and on a pressure envelope, information from the separate analyzers being shared for performance of the analysis techniques.

29. A blood pressure measurement system comprising:

a kiosk;

a blood pressure interface coupled to the kiosk and capable of detecting a pressure signal;

a microphone coupled to the blood pressure interface and capable of detecting an audio signal; and a blood pressure analyzer coupled to the kiosk, the blood pressure interface, and the microphone, the blood pressure analyzer including a plurality of separate analyzers that detect blood pressure using a plurality of separate analysis techniques, each of the plurality of analysis techniques being based on only one of audio signals, pressure oscillations, and a pressure envelope.

* * * * *